United States Patent [19]

Sioud

[11] Patent Number: 6,040,159
[45] Date of Patent: Mar. 21, 2000

[54] TNF-α RIBOZYMES AND DERIVATIVES CAPABLE OF DECREASING DEGRADATION OF MRNA IN VIVO

[75] Inventor: Mouldy Sioud, Oslo, Norway

[73] Assignee: Gene Shears Pty. Limited, Canberra, Australia

[21] Appl. No.: 08/416,516

[22] Filed: Apr. 4, 1995

Related U.S. Application Data

[63] Continuation of application No. 07/971,058, Nov. 3, 1992, abandoned.
[51] Int. Cl.$^7$ .......................... C12P 19/34; C07H 21/04; C12N 15/85; C12N 1/20
[52] U.S. Cl. .................. 435/91.31; 435/91.1; 435/320.1; 435/325; 536/23.1; 536/23.2; 536/24.1; 536/24.5
[58] Field of Search .................................. 536/23.1, 23.2, 536/24.5; 435/91.31, 91.1, 33, 320.1, 325; 514/44; 535/33

[56] References Cited

U.S. PATENT DOCUMENTS

| | | | |
|---|---|---|---|
| 4,666,848 | 5/1987 | Gelfand et al. | 435/252.33 |
| 5,107,065 | 4/1992 | Shewmaker et al. | 300/205 |
| 5,149,635 | 9/1992 | Gillies | 435/69.1 |
| 5,254,678 | 10/1993 | Haseloff et al. | 536/23.2 |

FOREIGN PATENT DOCUMENTS

| | | |
|---|---|---|
| 8905852 | 6/1989 | WIPO . |
| 9207065 | 4/1992 | WIPO . |

OTHER PUBLICATIONS

Baralle, F.E. (1983) The Functional Significance of Leader and Trailer Sequences in Eukaryotic mRNAs. International Rev. of Cytology 81:71–106.
Beutler, B. and Cerami, A. (1989) The Biology of Cachectin/TNF–A Primary Mediator of the Host Response. Ann. Rev. Immunol. 7:625–655.
Elela, S.A. and Nazar, R.N. (1992) Extended Secondary Structure as a Basis of Increased RNA Stability in a thermophilic alga Cyanidium caldarium. Biochimica et Biophysica Acta. 130:339–342.
Haseloff, J. and Gerlach, W.L. (1988) Simple RNA Enzymes with New and Highly Specific Endoribonuclease Activities. Nature 334:585–591.
Hsu, Y.–P. and Schimmel, P. (1984) Yeast LEU1. J. Biol. Chem. 259(6):3714–3719.
Nielsen, D.A. and Shapiro, D.J. (1990) Insights into Hormonal Control of Messenger RNA Stability. Mol. Endo. 4(7):953–957.
Perreault, J. et al. (1990) Mixed deoxyribo–and ribo–oligonucleotides with catalytic activity. Nature 344:565–567.
Proudfoot, N.J. and Brownlee, G.G. (1976) 3' Non–coding Region Sequences in Eukaryotic Messenger RNA. Nature 263:211–214.
Ross, H.J. et al. (1991) Cytokine Messenger RNA Stability is Enhanced in Tumor Cells, Blood 77(8):1787–1795.
Rossi, J.J. et al. (1992) Ribozymes as Anti–HIV–1 Therapeutic Agents: Principles, Applications, and Problems. AIDS Research and Human Retroviruses 8(2):183–189.
Saini, K.S. et al. (1990) Molecular Events Regulating Messenger RNA Stability in Eukaryotes. Mol. and Cell. Biochem. 96:15–23.
Shaw, G. and Kamen, R. (1986) A Conserved AU Sequence from the 3' Untranslated Region of GM–CSF mRNA Mediates Selective mRNA Degradation. Cell 46:659–667.
Sioud, M. and Drlica, K. (1991) Prevention of Human Immunodeficiency Virus Type I Integrase Expression in *Escherichia coli* by a Ribozyme. Proc. Natl. Acad. Sci. U.S.A. 88:7303–7307.
Sioud, M. et al. (1992) Preformed Ribozyme Destroys Tumor Necrosis Factor mRNA in Human Cells. J. Mol. Biol. 223:831–835.
Zaret, K.S. and Sherman, F. (1984) Mutationally Altered 3' Ends of Yeast CYC1 mRNA Affect Transcript Stability and Translational Efficiency. Mol. Biol. 176:107–135.
Grosshans and Cech, (1991) "A hammerhead ribozyme allows synthesis of a new form of the Tetrahymena ribozyme homogeneous in length with a 3' end blocked for transesterification." *Nucleic Acid Research*, 19(14):3875–3880.
Kisich, K.O. and Erickson, K.L., (1991) "Anti–tumor necrosis factor–a mRNA within mammalian cells." *Journal of Leukocyte Biology*, Supp.2, p.70.
Cotten, Matt, (1990) "The in vivo application of ribozymes," *Elsevier Science Publishers Ltd.*, 8(7):174–178.
Sioud et al. (1992) J. Mol. Biol. vol. 223: 831–835.
Sioud et al. (1992) Scandinavian J. Immun. vol. 36(4): 640.
Kisich et al. (1991) J. Leukocyte Biol. vol. 50(Suppl): 70.
Pennica et al. (1984) Nature vol. 312: 724–729.

*Primary Examiner*—John S. Brusca
*Assistant Examiner*—Sean McGarry
*Attorney, Agent, or Firm*—John P. White; Cooper & Dunham LLP

[57] ABSTRACT

This invention describes compounds active against TNF-α mRNA. It further describes mRNA molecules capable of conferring stability to RNA in vivo. Possible mRNA molecules to be stabilized include ribozymes, antisense molecules and mRNA encoding polypeptides useful for protein production. The ribozymes and antisense molecules described herein are useful in mammals and plants, particularly suited for viral diseases. Methods of production and methods of use are also described.

10 Claims, 11 Drawing Sheets

Figure 3a
Figure 3b
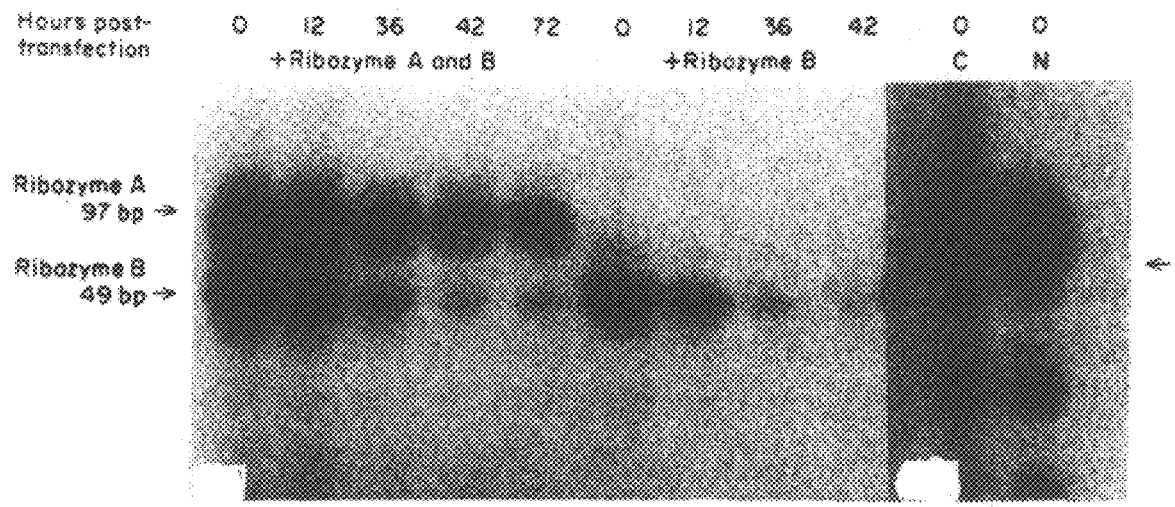
Figure 3c
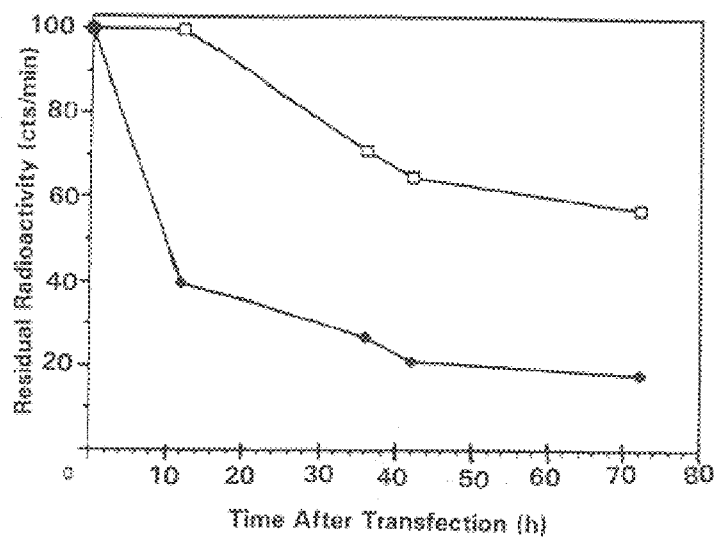

Figure 9

```
                    10           20                 interleukin 2
(Seq ID No.21)                                      ribozyme
  5'-GGUGCAAUGCAA    AUGA    G                      (IL2R)
               CUG      GUCC  U
               GAC      CAGG  G
   ----UUAAGAG     AAAG    A
            40           30
```

IL2R Linked
to TNF-R

```
            10           20           30           40
5'GGUGCAAUGCAA    AU   -C  ----GA     GAAA  --G    AAAA
(Seq ID No.22)  CUG  GAGU  CGU     GGAC   CA    GAGA
                GGU  CUCA  GCA     CCUG   GU    CUCU    G
  -------UUAA    -C   AA  GGAGUG   ---A  AGU    AGUA
                 80          70           60           50
```

IL2R Linked
to TNF-α
antisense

```
(Seq ID No.23)    10           20           30           40
  5'-GGUGCAAUGCAACUGAUGAG    GUGA    A    -A         AGUUA
                         UCC     GG CG    AACAGG
                         AGG     CC GU    UUGUCU          A
   ------------------UA    ---U  -  CA         AGUAG
                                               60     50
```

6,040,159

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: Other nucleic acid
       (A) DESCRIPTION: (Mixed DNA/RNA oligomer
            see specification and figures for details)

(xi) SEQUENCE DESCRIPTION: SEQ ID NO:1:

NAAGAUGAUC UCUGANGANN NNNNNNNNNN GAAACUGCCU GGN          43

(2) INFORMATION FOR SEQ ID NO:2:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: Other nucleic acid
       (A) DESCRIPTION: (Mixed DNA/RNA oligomer
            see specification and figures for details)

(xi) SEQUENCE DESCRIPTION: SEQ ID NO:2:

AAGAUCUACU GCCUGG                                        16

(2) INFORMATION FOR SEQ ID NO:3:

(i) SEQUENCE CHARACTERISTICS:
       (A) LENGTH: 42 base pairs
       (B) TYPE: nucleic acid
       (C) STRANDEDNESS: single
       (D) TOPOLOGY: linear (ii) MOLECULE TYPE: Other nucleic acid
       (A) DESCRIPTION: (Mixed DNA/RNA oligomer
            see specification and figures for details)

(xi) SEQUENCE DESCRIPTION: SEQ ID NO:3:

AAGAUGAUCU CUGAUGANNN NNNNNNNNNG AAACUGCCUG GN           42

(2) INFORMATION FOR SEQ ID NO:4:

(i) SEQUENCE CHARACTERISTICS:
       (A) LENGTH: 42 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:4:

AAGAUGAUCU CUGAUGAGUC CGUGAGGACG AAACUGCCUG GN           42

(2) INFORMATION FOR SEQ ID NO:5:

(i) SEQUENCE CHARACTERISTICS:
       (A) LENGTH: 43 base pairs
       (B) TYPE: nucleic acid

```
            (C) STRANDEDNESS: single
            (D) TOPOLOGY: linear (ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:5:

NAAGAUGAUC UCUGANGANN NNNNNNNNNN GAAACUGCCU GGN                      43

(2) INFORMATION FOR SEQ ID NO:6:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:6:

NAAGAUGAUC UGACUGCCUG GN                                             22

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:7:

AAGAUGAUCU ACUGCCUGG                                                 19

(2) INFORMATION FOR SEQ ID NO:8:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:8:

NNCUGANGAN NNNNNNNNNN NGAAAN                                         26

(2) INFORMATION FOR SEQ ID NO:9:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:9:

GUGCAAUGCA ACUGAUGAGU CCGUGAGGAC GAAACAGGAG AAAAAGAUGA UCUCUGAUGA    60

GUCCGUGGGG ACGAAACUGC CUGGAAUU                                       88

(2) INFORMATION FOR SEQ ID NO:10:

(i) SEQUENCE CHARACTERISTICS:
            (A) LENGTH: 87 base pairs
            (B) TYPE: nucleic acid
```

(C) STRANDEDNESS: single
            (D) TOPOLOGY: linear (ii) MOLECULE TYPE: RNA (genomic)

(xi) SEQUENCE DESCRIPTION: SEQ ID NO:10:

GAAAUGAUCU CUGAUGAGUC CGUGAGGACG AAACUGCCUG GAAAUGCAAU GCAACUGAUG      60

AGUCCGUGAG GACGAAACAG GAGAAUU      87

(2) INFORMATION FOR SEQ ID NO:11:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:11:

GGUGCAAUGC AACUGAUGAG UCCGUGAGGA CGAAACAGGA GAAUUGAUGA UCUGACUGCC      60

UGGAAUU      67

(2) INFORMATION FOR SEQ ID NO:12:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:12:

GGAUGAUCUG ACUGCCUGGA AUUGUGCAAU GCAACUGAUG AGUCCGUGAG GACGAAACAG      60

GAGAAUU      67

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:13:

NNCUGANGAN GAAAN      15

(2) INFORMATION FOR SEQ ID NO:14:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:14:

GAUGAUCUCU GAUGAGUCCG UGAGGACGAA ACUGCCUGGU GCAAUGCAAC UGAUGAGUCC      60

GUGAGGACGA AACAGGAGAA AAA      83

(2) INFORMATION FOR SEQ ID NO:15:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:15:

GAGUACUAAG AUGAUCUCUG AUGAGUCCGU GAGGACGAAA CUGCCUGGUC UAGACAUAAC      60

CCCUUGGGGC CUCUAAACGG GUCUUGAGGG UUUUUUC                              97

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:16:

UCUGGCCCAG GCAGUCAGAU CAUCUUCUCG AAC                                  33

(2) INFORMATION FOR SEQ ID NO:17:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:17:

GAGUACUAAG AUGAUCUCUG AUGAGUCCGU GAGGACGAAA CUGCCUGGUC UAG            53

(2) INFORMATION FOR SEQ ID NO:18:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:18:

GUAAGAUGAU CUCUGAUGAG UCCGUGAGGA CGAAACUGCC UGAAUU                    46

(2) INFORMATION FOR SEQ ID NO:19:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AACAGCTGTA ATACGACTCA CTATAGAGTA CTAAGATGAT CTCTGATGAG TCCGTGAGGA      60

CGAAACTGA                                                              69

(2) INFORMATION FOR SEQ ID NO:20:

(i) SEQUENCE CHARACTERISTICS:
    (A) LENGTH: 72 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:20:

TTCTCGAGAA AAAACCCTCA AGACCCGTTT AGAGGCCCCA AGGGGTTATG TCTAGACCAG    60

GCAGTTTCGT CC    72

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AACAGCTGTA ATACGACTCA CTATAGAGTA CTAAGATGAT CTGACTGCCT GGTCTAG    57

(2) INFORMATION FOR SEQ ID NO:22:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TTCTCGAGAA AAAACCCTCA AGACCCGTTT AGAGGCCCCA AGGGGTTATG TCTAGACCAG    60

CA    62

(2) INFORMATION FOR SEQ ID NO:23:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:23:

GGUGCAAUGC AACUGAUGAG UCCGUGAGGA CGAAACAGGA GAAUUNNNN    49

(2) INFORMATION FOR SEQ ID NO:24:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:24:

GGUGCAAUGC AACUGAUGAG UNCCGUNNNN GAGGACGAAA CANNGGAGAA AAAGAUGAUC    60

UCUGAUGANN NGUCCGUGAG GACGAAACUC CNUGGAAUUN NNNNNN    106

(2) INFORMATION FOR SEQ ID NO:25:

(i) SEQUENCE CHARACTERISTICS:
       (A) LENGTH: 90 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:25:

GGUGCAAUGC AACUGAUGAG UCCGUGAGGA CGNAAACAGG AGUUAAGAUG AUCUGUUACU         60

GNCCUNNNGG AAUNNNNNNN NNNNNNNNNN                                         90

(2) INFORMATION FOR SEQ ID NO:26:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:26:

AAGATUGAUU CTUCUGAUGA NNNNNNNNNN NGAAACTUGC CTUGGN                        46

TNF-α RIBOZYMES AND DERIVATIVES CAPABLE OF DECREASING DEGRADATION OF MRNA IN VIVO

This is a continuation of application Ser. No 07/971,058, filed Nov. 3, 1992 and now abandoned.

BACKGROUND OF THE INVENTION

Throughout this application various publications are referred by arabic numerals to within brackets. The disclosures for these publications in their entireties are hereby incorporated by reference into this application to more fully describe the state of the art to which this invention pertains.

The discovery of RNA molecules that possess enzymatic, self-cleaving activity (ribozymes) has provided a new way to artificially control gene expression (Foster & Symons, (1987) Cell, 49: 585–591). Ribozymes have been designed that contain nearly all of the sequences required for cleavage. For the hammerhead type the target RNA needs to contain only the sequence XUX with cleavage occurring 3' from XUX (Haseloff & Gerlach, (1988) Nature, (London) 334: 585–591; Perriman et al., Gene (1992) 113: 157–163). The high specificity and limited target requirement give these catalytic RNA molecules the potential for inhibiting viral pathogens and for regulating specific gene expression by interfering with transcription in a highly specific manner (Uhlenbeck, (1987) Nature (London) 328: 596–600; Haseloff & Gerlach, (1988) Nature, (London) 334: 585–591).

Several reports indicate that the hammerhead type of ribozyme functions in living cells. Cotten & Birnstiel (1989, EMBO J., 8: 3861–3866) and Cameron & Jennings (1989, Proc. Natl. Acad. Sci., USA 86: 9139–9143) reported ribozyme-mediated destruction and lowering of specific gene expression in *Xenopus laevis* oocytes and monkey (COS1) cells, respectively. Sarver et al. (1990, Science, 247: 1222–1225) showed that a ribozyme directed against HIV-1 gag RNA reduced p24 antigen expression in CD4+ HeLa cells. Recently, this line of study was extended to bacterial cells by showing that a ribozyme designed to cleave the integrase gene of HIV-1 is effective when transcribed from a plasmid in *Escherichia coli*. Integrase RNA was eliminated and integrase protein synthesis was blocked (Sioud & Drlica, (1991) Proc. Natl. Acad. Sci., USA 88: 7303–7307). Since ribozymes are effective in vivo, problems of ribozyme stability and delivery may now be addressed.

To interfer with tumour necrosis factor α (TNF-α) gene expression we have used cationic liposome-mediated transfection (Malone et al., (1989) Proc. Natl. Acad. Sci., USA 86: 6077–6081) to deliver a ribozyme directed against TNF-α into human promyelocytic leukaemia cells (HL60) and peripheral blood mononuclear cells (PBMNC). TNF-α plays an important role in many inflammatory rheumatic diseases (Shinmei et al., (1989) Sem. Arth. Rheum. 18 (suppl. 1) 27–32), and it modulates the expression of several proteins, including the class I antigens of the major histocompatibility complex (MHC) and cytokines such as interleukin 1 and interleukin 6 (Beutler & Cerami, (1988) Annu. Rev. Biochem. 57: 505–518 and (1989) Annu. Rev. Immunol. 7: 625–655). TNF-α also appears to be necessary for normal immune responses, but large quantities of it can produce destructive effects such as those seen in rheumatoid arthritis (Brennan et al., (1989) Lancet ii 244–247). In addition, TNF-α is the cytokine responsible for the induction of HIV-1 expression in ACH-2 cells (Rosenberg & Fauci, (1990) Immunol. Today 11: 176–180). TNF-α induces the production of cellular factors that bind to the NF-κB enhancer elements within the viral long terminal repeat sequences and thereby activates HIV-1 expression.

The effectiveness of catalytic RNA molecules is dependent on the stability of the mRNA in vivo. In comparison with the knowledge of DNA structural elements, little is known about mRNA stability elements. m-RNA half-lives range from less than 30 minutes for fibroblast interferon and c-fos to greater than 17 hours for β globin. Most eukaryotic mRNAs are protected in cells from exonuclease attack by the 5' cap structure and the 3'poly(A) tail and poly(A) binding proteins. In addition, eukaryotic mRNAs have both 5' and 3' non-coding regions on either side of the coding region. The 5' non-coding region is involved in the rate of initiation of translation of the mRNA to protein. The 3' non-coding region serves to initiate the formation of the poly(A) and can act to stabilize mRNA. (Baralle, F. E., Int. Rev. of Cytology (1983) 81: 71–106.) In particular, 3' non-coding iron-responsive elements have been identified that modulate mRNA stability in the presence of iron. Another characterized motif is the AUUUA element responsible for the rapid degradation of some cellular mRNAs, particularly cytokine mRNAs. (Saini, K. S. et al., Mol. Cel. Biochem. (1990) 96: 15–23; Ross, H. J. et al., Blood (1991) 77: 1787–1795). Some have postulated that an initial endonuclease attack is required, before rapid degradation can take place (Nielson, D. A. and Shapiro, D. J., Mol. Endocrinology (1990) 4: 953–957).

There is a need for methods to extend the half-life of particular mRNAs in vivo for protein production and oligonucleotide methods of gene control (antisense and triple helix) for use in plants and animals. Further, stabilizing mRNA elements can be applied to ribozymes in addition to antisense oligonucleotides.

SUMMARY OF THE INVENTION

This invention describes compounds active against TNF-α mRNA. It further describes mRNA molecules capable of conferring stability to RNA in vivo. Possible mRNA molecules to be stabilized include ribozymes, antisense molecules and mRNA encoding polypeptides useful for protein production. The ribozymes and antisense molecules described herein are useful in mammals and plants, particularly suited for viral diseases. Methods of production and methods of use are also described.

Ribozyme A is composed of the conserved ribozyme sequence as described by Haseloff & Gerlach (1988), the 5' and 3' flanking sequences complementary to the TNF-α RNA nucleotides 374 and 393: see Pennica et al., (Nature (1984) 312: 724–729) for numbering and bacteriophage T7 transcription terminator with CU mispair (C) (Rosenberg et al., Gene (1987) 56: 125–135). Ribozyme B is identical to A except that it lacks the T7 transcription terminator. Ribozyme II is a shortened version of ribozyme B with 9 and 11 base pair hybridizing arms. Antisense RNA is identical to ribozyme A except that it has a single guanosine nucleotide in place of the catalytic domain. The anti-TNF-α hammerhead catalytic gene and antisense RNA control were made as described by Sioud & Drlica ((1991) Proc. Natl. Acad. Sci., USA 88: 7303–7307). Briefly, 2 overlapping half oligonucleotides containing the sequences of a bacteriophage T7 RNA polymerase promoter, the 5' and 3' recognition sequences of the ribozyme, the catalytic domain and the T7 transcription terminator were synthesized (an XbaI restriction site was introduced between the T7 terminator and the 3' end of the ribozyme, and PruII and XhoI sites at the 5' and 3' ends of the ribozyme sequences, respectively), hybridized and then extended with the Klenow fragment of DNA polymerase. Following the extension, DNA was extracted with phenol, precipitated with ethanol, gel purified and then cloned into a SmaI cleaved pUC 18 vector. The sequences of the overlapping primers (Public Health Research Institute, New York 10016, N.Y.) used as follows:

(1) Ribozyme primers: (SEQ. ID.: 19–22)

5'AACAGCTGTAATACGACTCACTATAGAG-TACTAAGATGATCTCTGATGAGTCCGTG AGGACGAAACTGC3' and

5'TTCTCGAGAAAAAACCCTCAAGAC-CCGTTTAGAGGCCCCAAGGGGTTATGTCTAGA CCAGGCAGTTTCGTCC3'

(2) Antisense primers:

5'AACAGCTGTAATACGACTCACTATAGAG-TACTAAGATGATCTGACTGCCTGGTCTA G3' and

5'TTCTCGAGAAAAAACCCTCAAGAC-CCGTTTAGAGGCCCCAAGGGGTTATGTCTAGA CCAGCA3'.

The underlined sequences resulted from the presence of restriction sites in the DNA template. Ribozyme II, unlike ribozyme A and B, lacks these sequences. Therefore, the restriction sequences are not required for stability. Yet, all three of these ribozymes are stable in vivo and bind protein.

Figure 2A:
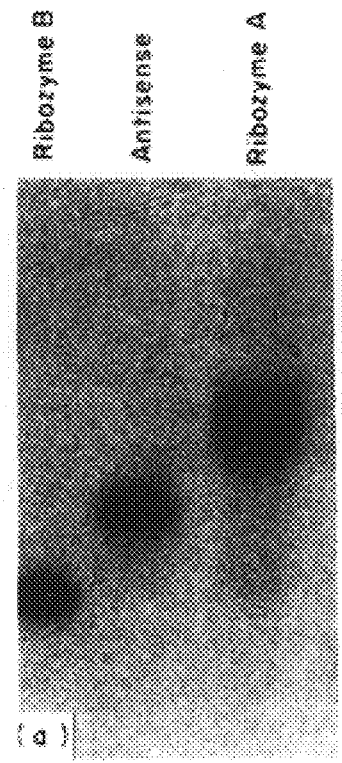
Figure 2B:
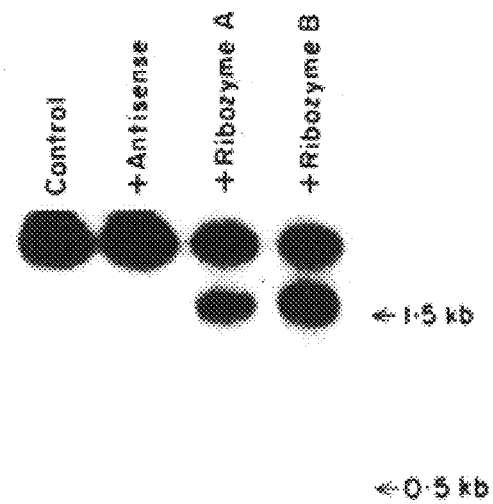

FIGS. 2a–2b: (2a) In vitro RNA transcripts and (2b) in vitro activity (2a) In vitro transcription of ribozymes A, B and TNF-α antisense. Ribozymes and antisense RNA were transcribed with T7 RNA polymerase from PAGE-purified template DNA fragments cleaved from recombinant plasmids as described by (Uhlenbeck, O., Nature (1987) 328: 596–600). RNA was labelled internally with [α$^{32}$P]CTP during transcription. Transcription was primed with 7-methyl guanosine (5') triphospho (5') guanosine in all cases. Transcripts were treated with DNAse (RNAse-free), extracted with phenol, precipitated with ethanol and then analyzed by electrophoresis in a 15% polyacrylamide gel containing 7 M-urea. The lengths of ribozymes A, B and antisense are 97, 49 and 76 nucleotides, respectively. (2b) Cleavage of TNF-α RNA by PMA and ConA to express TNF-α whole cell RNA was extracted and the RNA (20 μg) was incubated with 1 μg of either ribozyme or antisense RNA for 60 min. at 50° C. RNA species were then separated by gel electrophoresis and TNF-α RNA was identified by Northern blotting (kb=10$^3$ bases).

FIGS. 3a–3c. Ribozyme stability following transfection.

The effect of bacteriophage T7 transcription terminator on RNA stability was compared by cotransfecting HL60 cells with ribozymes A and B. Total RNA was extracted and analyzed by electrophoresis in 15% (w/v) polyacrylamide gels containing 7 M-urea. While ribozyme A could be detected more than 72 hours post transfection, the amount of ribozyme B progressively declined (FIG. 3(a). The radioactivity contained in each band was then determined, and the results were expressed as the percentage of the radioactivity at zero time. FIG. 3(c) shows that ribozyme B decays more rapidly than ribozyme A. The residual radioactivity for ribozyme A and B 72 hours post transfection was 57% and 18% respectively. The stability of the antisense RNA control (ribozyme A lacking the catalytic domain) is similar to ribozyme A (data not shown). Thus, the addition of a bacteriophage T7 terminator to the 3' end of a ribozyme increases it stability.

The compartmentalisation of ribozyme A in HL60 cells was also studied by analysis of cytoplasmic and nuclear RNAs. As shown in FIG. 3(b) (lanes N and C), ribozyme A is preferentially located in the nucleus.

Ten million human HL60 cells (ATCC CCL 240), growing in log phase in RPMI 1640 supplemented with 20% (v/v) fetal calf serum (FCS), were used for RNA transfection. Cells were washed twice with serum-free medium. A drop (5 ml) of serum free medium was added to polystyrene tubes followed by 35 μg of lipofectin (Bethesda Research Laboratories). 10 μg of carrier RNA (E. coli. tRNA). 3×10$^6$ disints min of $^{32}$p-labelled capped ribozyme A, B or antisense RNA (5 μg). The mixture was immediately mixed. The cells were resuspended in a mixture of serum-free medium lipofectin/RNA/carrier RNA and returned to the incubator for 20 h. Following transfection cells were washed 3 times with Hank's buffered saline solution and then returned to the incubator with RPMI supplemented with 20% FCS. Cells (10$^6$) were harvested at the times indicated above each lane, and total RNA was prepared and analyzed by 15% polyacrylamide gel with 7 M-urea. The RNA samples used for transfection are indicated at the top of FIG. 3. Ribozyme B alone serves as a marker to indicate its position in co-transfection experiments. (b) Analysis of nuclear (N) and cytoplasmic (C) RNA. A sample (50 μM) of labelled, capped ribozyme A was used to transfect HL60 cells for 20 h. Cells were washed 3 times, and the nuclear and cytoplasmic RNAs were prepared and analyzed by gel electrophoresis. For preparation of cytoplasmic and nuclear fractions, the cells were homogenized in 10 mM-Tris.HCl (pH 7.5). 5 mM-KCl, 140 mM-NaCl, 5 mM-dithiothreitol and 0.49% (w/v) Nonidet P40 for 10 min at 4° C. and the nuclei were collected by centrifugation at 800 g for 5 min. RNA in the supernatant fluid was precipitated and saved as the cytoplasmic fraction. The nuclei were processed as described by Chomezynski & Sacchi (1987, Anal. Biochem. 162: 156–160) for total RNA preparation. The arrow indicated the position of ribozyme A monomer. (c) one experiment showing RNA quantification. The run amount of radioactivity in the ribozyme bands shown in (a) was determined and expressed as a percentage of the radioactivity present immediately after 20 h transfection time. □ Ribozyme A: ♦ ribozyme B.

Figure 4:
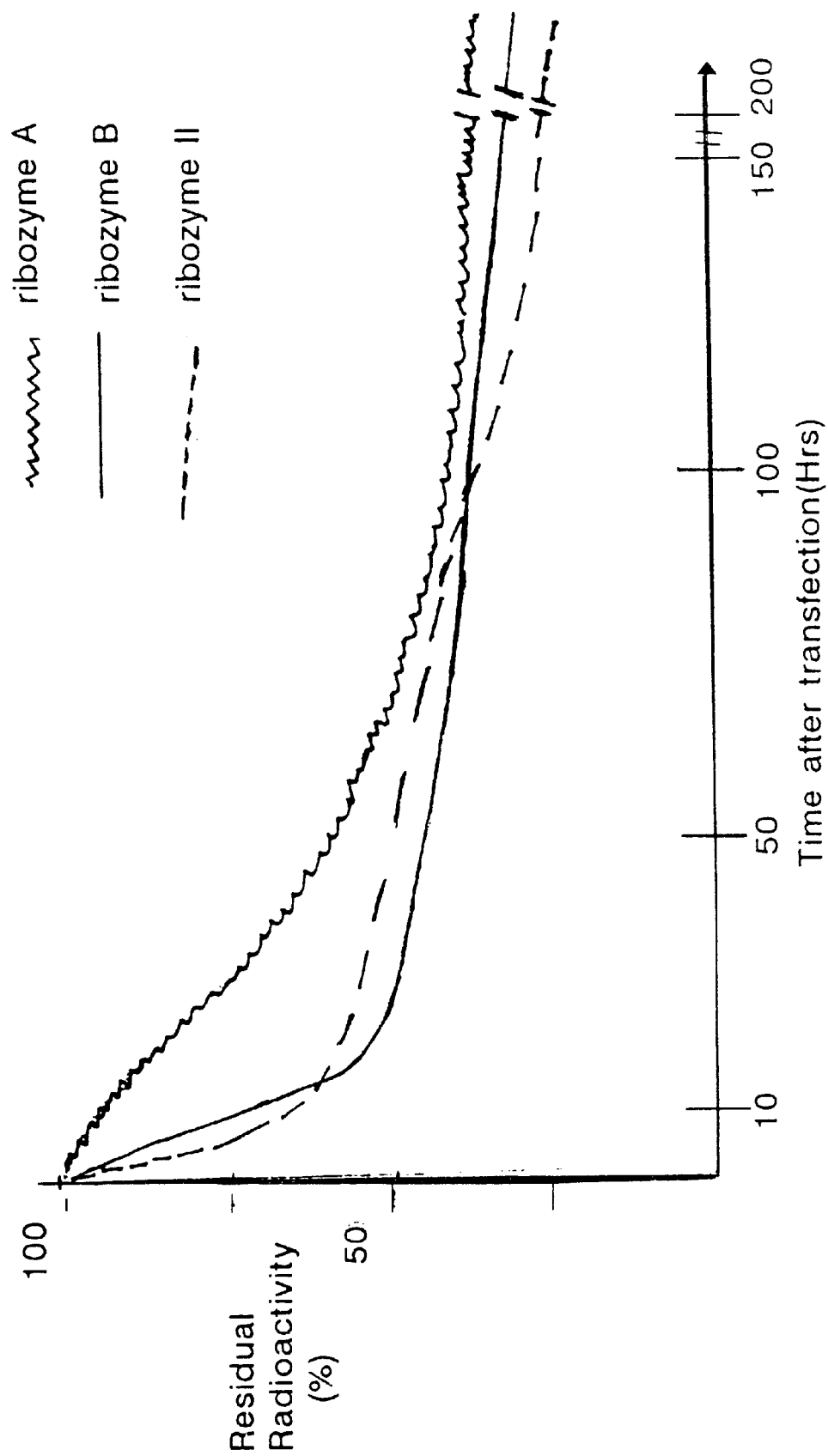

FIG. 4: Stability of ribozyme A, B and II in HL60 cells.

Mean of more 50 experiments, ribozymes were introduces to the cells using the DOTMA cationic liposome-mediated transfection. Following transfection cells were washed and resuspended in complete media. Cells contained in 1 ml culture were harvested at various times. Total RNA was prepared and then analyzed by 15% polyacrylamide gel containing 7 M urea. The amount of ribozyme radioactivity was normalized to actin mRNA or ribosomal RNA and then expressed as a percentage of the radioactivity present after 16 hours post-transfection time. These experiments were repeated 50 times at each time point as opposed to FIG. 3(c) which was just a single experiment. Further, reexamination of FIG. 3(c) showed parallel curves for ribozyme A and B indicating similar stability for ribozyme B.

Figure 5A:
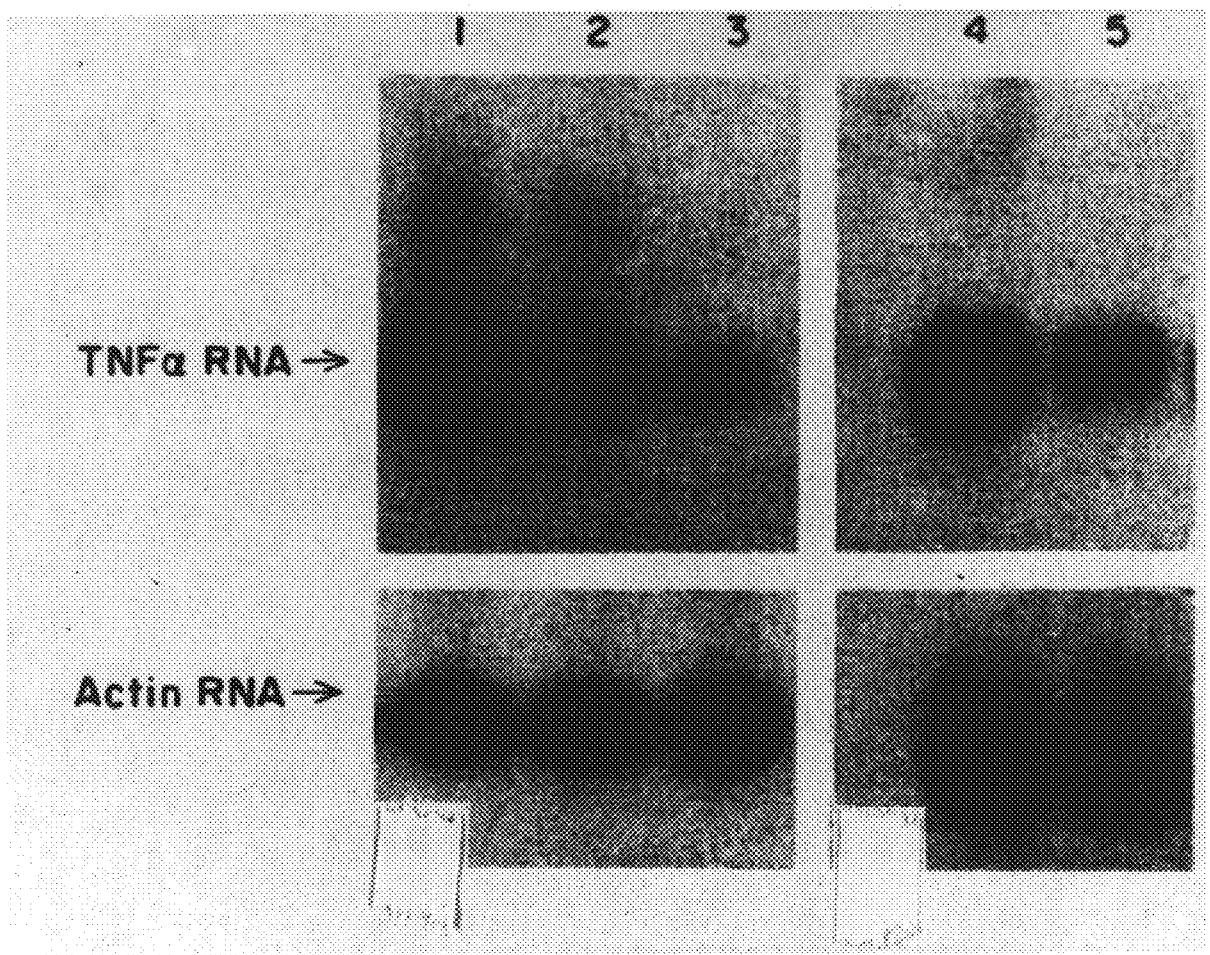
Figure 5B:
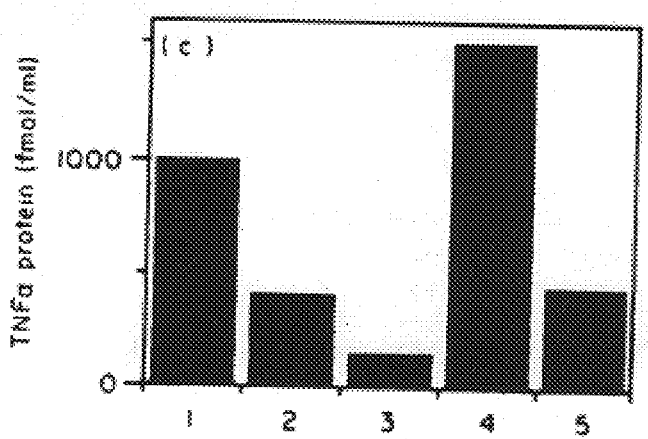

FIGS. 5a–5b. Ribozyme activity in vivo.

Ribozymes and antisense RNA activities in HL60 cells (5a) were analyzed after a transfection period (20 h). Following transfection with ribozyme A or antisense RNA, cells were stimulated for 6 h to express TNF-α. RNA was extracted, separated by gel electrophoresis through a 1–2% (w/v) agarose form-aldehyde gel, and detected by Northern blotting with radioactive probe for the TNF-α gene. After hybridization with TNF-α probe, the filter was stripped and then hybridized with an actin probe (British Biotechnology Limited), in the case of PBMNC. Cells were separated (Sioud et al., 1990) and washed 4 times with Hank's buffered saline solution and 3 times with serum-free medium. Cells ($10^6$) were transfected and processed as HL60 cells. Lanes 1 and 4, controls (transfected only with carrier RNA); lane 2, antisense RNA; lanes 3 and 5, ribozyme A. This auto-radiogram was overexposed to display the TNF-α signal in ribozyme A lanes. (5b) Radioimmunoassay to TNF-α protein. The amount of TNF-α protein present in the media was determined using the TNF-α [$^{125}$I] assay system (Amersham). Lanes 1 to 5 correspond to lanes 1 to 5 in FIG. 3(a) and (3b), respectively.

Figure 6A:
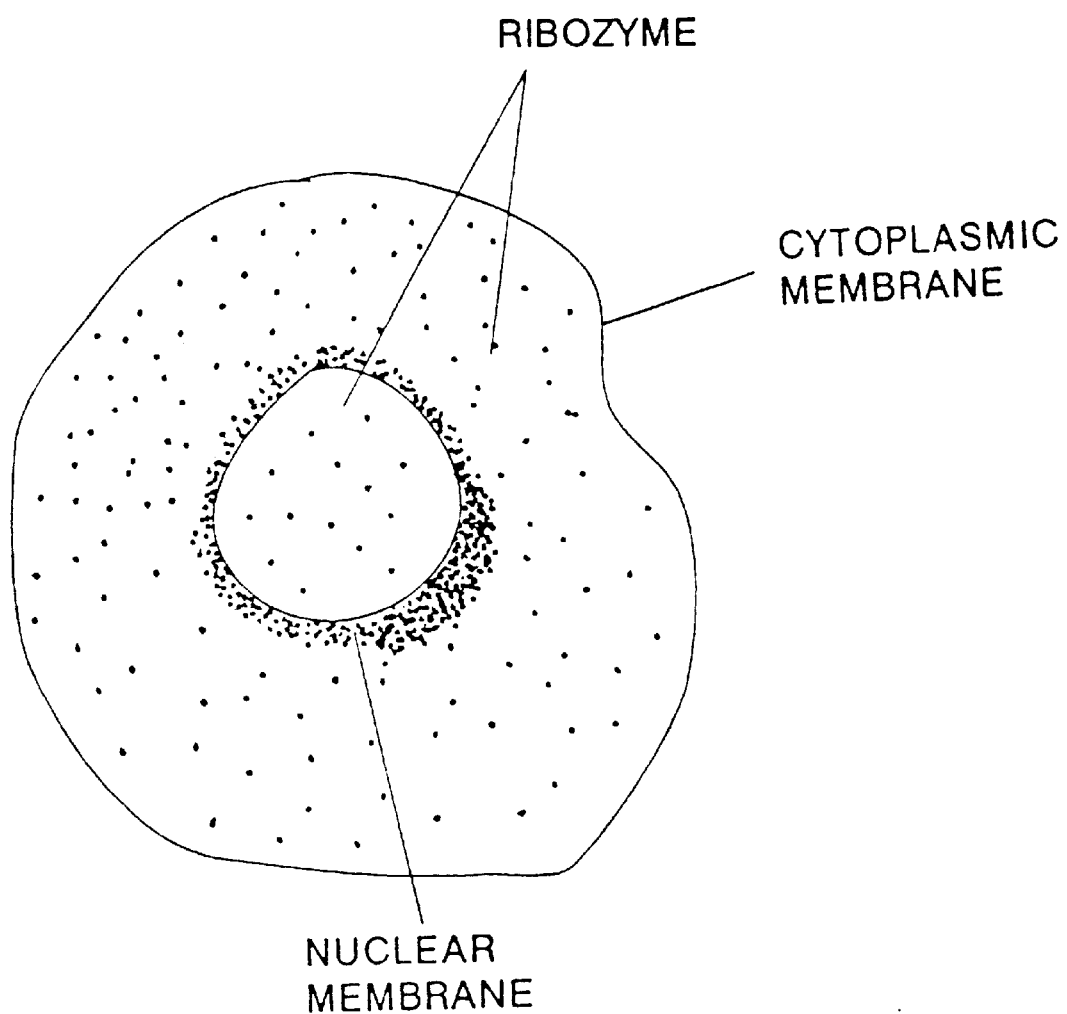
Figure 6B:
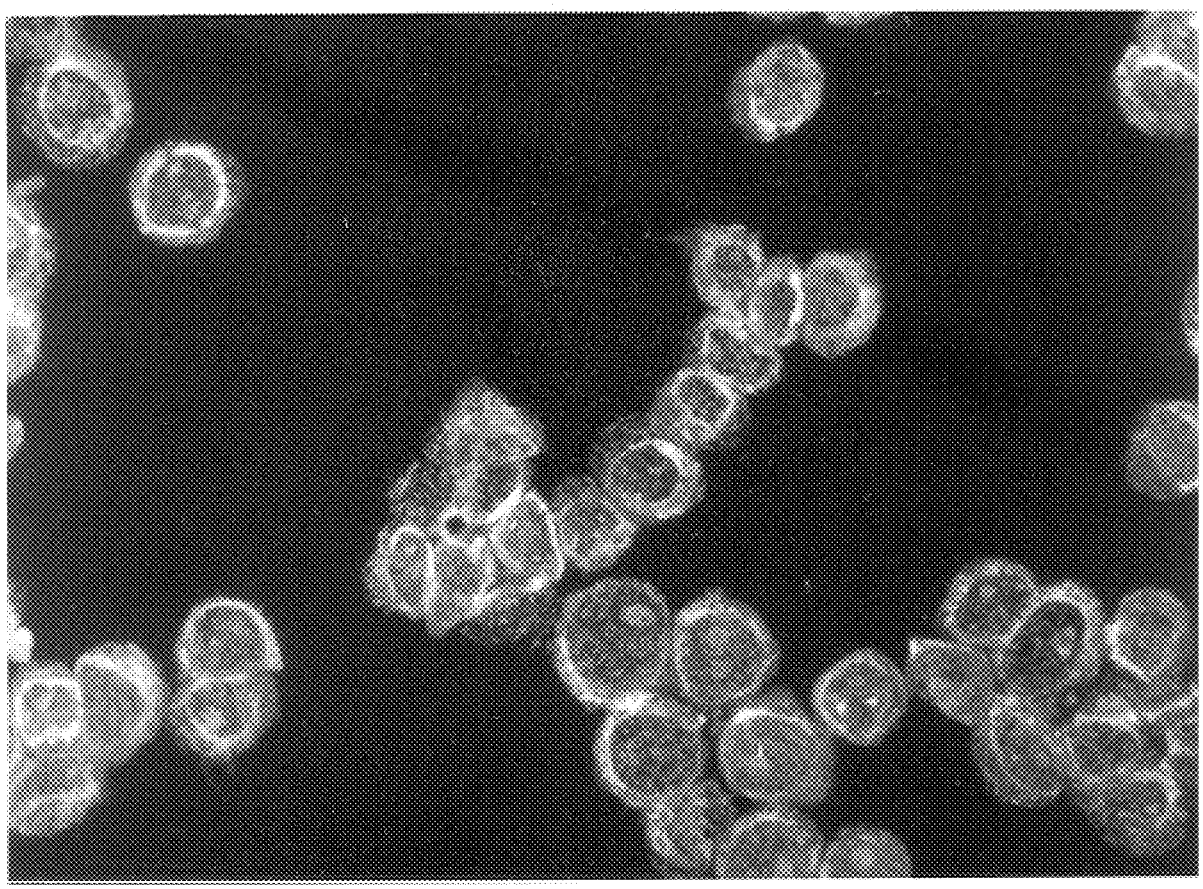

FIGS. 6a–b: Immunostaining of the ribozyme B and II in HL60 cells.

FIG. 6a shows digoxigenin conjugated uridine was incorporated into the ribozymes during transcription. Cells were transfected with Digoxigenin-conjugated ribozymes. Following transfection microscope slides were prepared and then the ribozyme inside the cells were detected with anti-Digoxigen-fluorescein Fab conjugate. FIG. 6b shows a photo of the fluorescent cells.

Figure 7A:
Figures 7B, 7C:
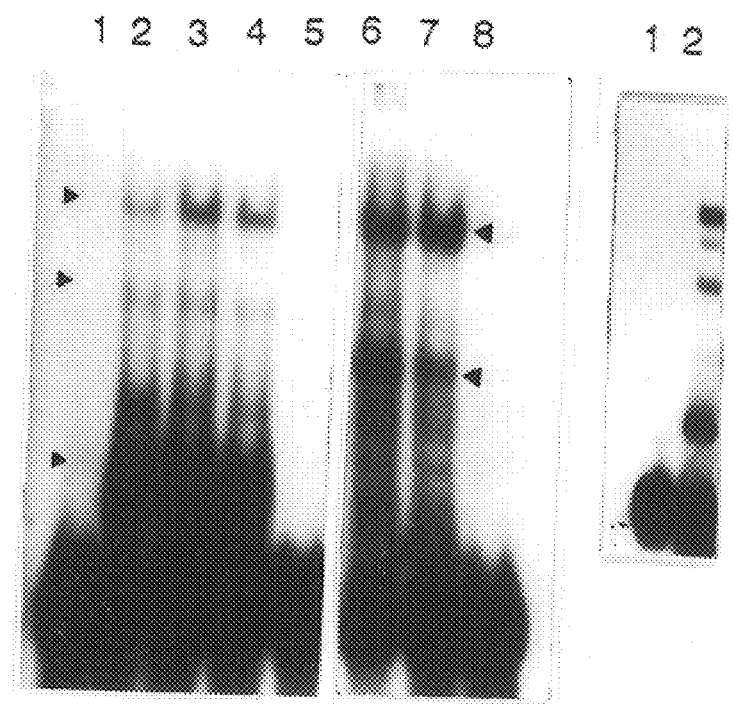

FIGS. 7a–c: Gel retardation assay of cytoplasmic extracts from HL60 cells and PBMNC with TNF-α ribozymes II and B.

7a) Ribozyme II was incubated (lanes 2,3,4 and 5) (see below) or not (lane 1) with extract proteins an then analyzed by electrophoresis. Lanes 4 and 5 are as lanes 2 and 3 respectively, but 20 units of RAsin was added. All complexes seen in lanes 4 and 5 could be seen in lanes 2 and 3 (original film).

7b) 25 ng of TNF-α ribozyme II was generated by in vitro transcription as described previously (Sioud, et al., 1992) was incubated at room temperature for 25 minutes with cytoplasmic extracts (CE) prepared from HL60 or PBMN cells as described in materials and methods. Following incubation the protein ribozyme complexes were separated by 4% polyacrylamide native gel. lane 1: control without CE; lane 2: +5 ug CE from HL60 cells; lane 3: as lane 2, but in addition 1 ug of tRNA was added; lane 4 as lane 3, but in addition 10 units of Rnase inhibitor was added; lane 5 as lane 4, but before electrophoresis the sample was treated with proteinase k; lane 6 as lane 1, but 5 ug of the CE from PBMN cells was added; lane 7 as lane 6, but more 1 ug of tRNA was added; lane 8 contains the ribozyme RNA recovered from the high molecular complex (The complex was excised from one preparative gel, the materials were eluted and then phenol extracted.

7c) gel retardation with ribozyme B: As panel A ribozyme B and incubated (lane 2) with 5 ug of CE prepared from HL60 cells.

Figure 8:
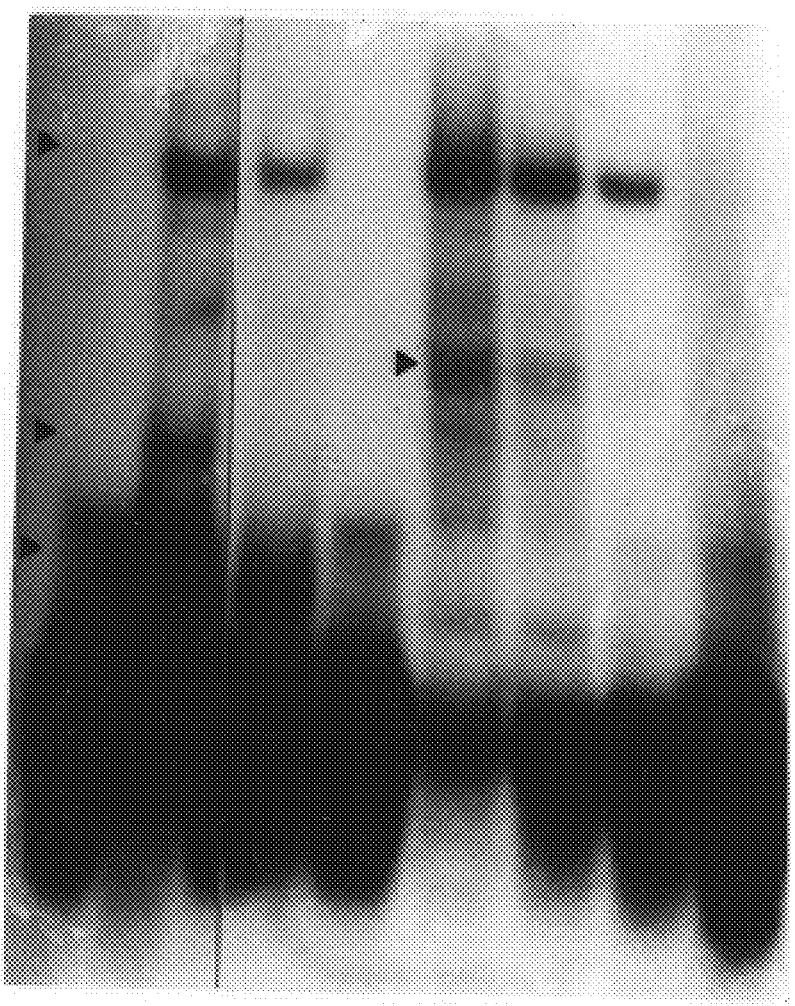

FIG. 8: Competition assays 25 ng of ribozyme II was incubated with 5 ug of cytoplasmic protein from HL60 cells or PBMN as described in FIG. 5. Lane 1 control without CE, lane 2 as lane 1, but both 5 ug of CE from HL60 cells and 2500 ng of polydCdI were added; lane 3 as lane2, but instead of polydC dI 2500 ng of cold ribozyme was added; lane 4 as lane 3, but 500 excess of cold ribozyme was added; lane 5 as lane 1, but 5 ug of CE from PBMN cells was added; lanes 6, 7, 8 as lane 5, but 300, 400 or 500 of cold ribozyme was added, respectively.

FIG. 9: Secondary structure of interleukin 2 (IL-2) ribozyme and IL-2 ribozyme linked to the 5 end of TNF-α ribozyme or antisense (SEQ. ID.: 23–25).

Figures 10A, 10B, 10C:
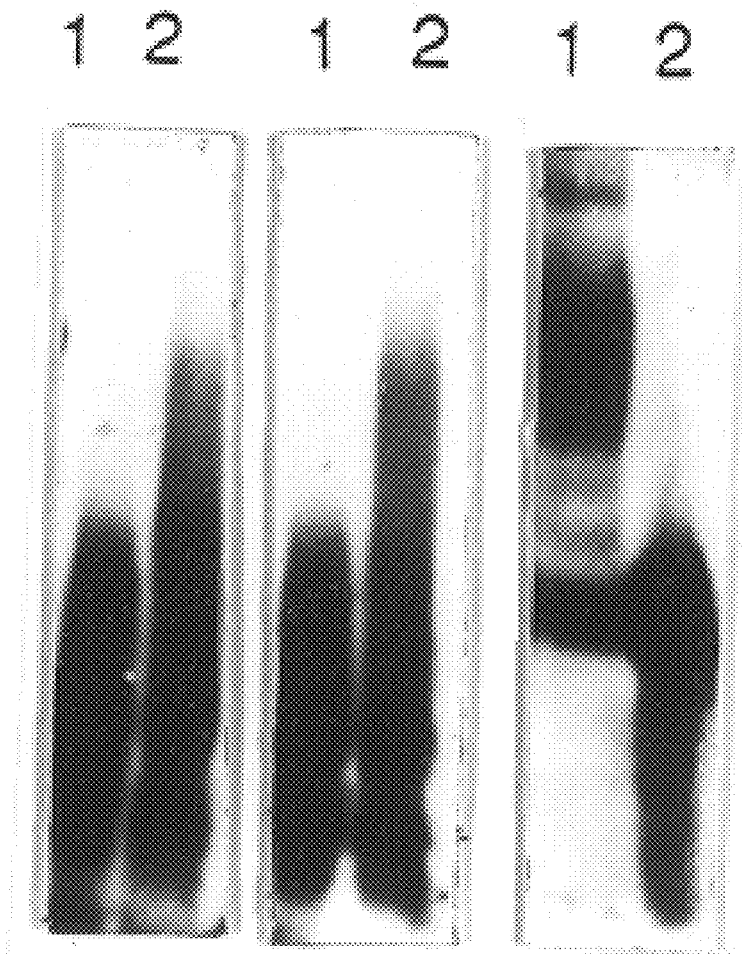

FIGS. 10a–10c: Gel retardation assay of cytoplasmic extract with IL-2 ribozymes.

10a) 25 ng of IL-2 ribozyme generated by in vitro transcription was incubated with CE from HL60 cells; lane 1 control without CE; lane 2 with CE from HL60 cells.

10b) Instead of CE with HL60 cells, IL-2 ribozyme was incubated with CE from PBNM cells (lane2).

10c) 25 ng of the chimeric ribozyme (IL-2 linked to TNF-α ribozyme) was incubated (lane1) or not (lane2) with cytoplasmic proteins from PBMN cells.

DETAILED DESCRIPTION OF THE INVENTION

The invention described herein relates to TFN-α ribozymes or compounds having the structure (SEQ ID NO: 1):

```
3'-(X)_n ggu(t)ccgu(t)cA            u(t)cu(t)agu(t)agaa(X)_n'-5'
              A                    C
              A                     \
              G                      U
              X   *   X              \
              X   *   X         (X)_a  G
              X   *   X         /      \
             (X)_m  *  (X)_m'   A        A
              X         X        \      /
               \       /          G —— X
               (X)_b
``` wherein each X represents a ribonucleotide or a deoxyribonucleotide which is the same or different and may be modified or substituted in its sugar, phosphate or base; wherein each of A, C, U, and G represents a ribonucleotide and a, c, u(t), and g represents a ribonucleotide or deoxyribonucleotide which may be unmodified or modified or substituted in its sugar, phosphate or base; wherein each of $(X)_n$ and $(X)_{n'}$ represents an oligonucleotide having a predetermined sequence; wherein each of n and n' represents an integer from 0 to 100; wherein each * represents base pairing between the nucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1 and typically less than 100; wherein each of the dashed lines independently represents either a chemical linkage providing covalent bonds between the nucleotides located on either side thereof or the absence of any such chemical linkage; and wherein $(X)_b$ represents an oligonucleotide which may be present or absent with the proviso that b represents an integer which is greater than or equal to 2 if $(X)_b$ is present.

Such compounds are targeted for cleaving the TNF-α mRNA in vivo. Site directed mutagenesis in the hybridizing arms ggu(t)ccgu(t)cA and u(t)cu(t)agu(t)agaa (SEQ ID NO: 2) is possible provided that sufficient complementarity is maintained for that the compound hybridizes to the TNF-α mRNA in vivo. All RNA compounds are also part of the invention also compounds with DNA arms and an RNA catalytic region.

Also part of the invention are compounds in which $(X)_n$ or $(X)_{n'}$ is absent. One form of the compound described above has the structure below (SEQ ID NO: 3):

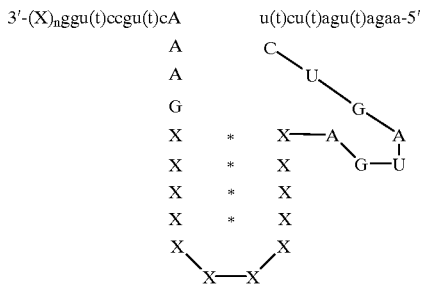

where the nucleotides are defined as above. An all RNA version of the compound is also described. Further the compound may have the structure (SEQ ID NO: 4):

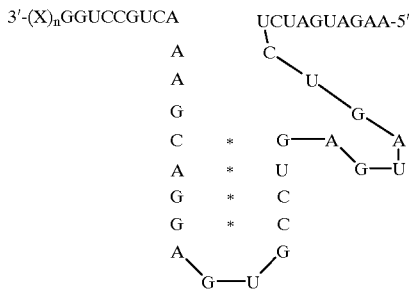

wherein (X)n represents an oligoribonucleotide.

The invention further includes a compound a multiple ribozyme having the structure:

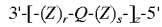

wherein each Q represents the compound of claim 1 which may be the same or different; wherein each Z represents a ribonucleotide or a deoxyribonucleotide which is the same or different and may be modified or substituted in its sugar, phosphate or base; wherein each of r and s represents an integer which may be greater than or equal to 0; and wherein z represents an integer greater than or equal to 1.

Further this invention relates to compounds and methods for increasing protein production by increasing the steady state level of mRNA by decreasing the rate of intracellular degradation of an mRNA of interest. Such compounds and methods are useful for increasing the stability, and therefore effectiveness, ribozymes and antisense RNA. The compounds and methods of this invention also can be utilized to increase the production of proteins by increasing the quantity of mRNA available to be transcribed.

Ribozymes are RNAs capable of catalyzing RNA cleavage reactions. One simplest and most commonly used are the hammerhead type ribozymes which contain a conserved catalytic domain and flanking sequences that hybridize with the substrate RNA (Haseloff et al. PCT International Publication No WO 89/05852). Hammerhead ribozymes can be targeted against any RNA sequence that contain an XUX triplet amenable for cleavage. Several studies have demonstrated the ability of these ribozymes to cleave a target RNA in vivo and suppress protein expression. Other classes of ribozymes are tetrahymena IVS (Group I Intron) (Cech et al. U.S. Pat. No. 4,740,463, issued Apr. 26, 1988), RNAse P (Altman et al. PCT International Publication No WO 92/03566) and hairpin ribozymes (Hampel et al. Nuc. Acids Res. (1990) 18: 299–304).

The stabilized mRNAs of the claimed invention may be further stabilized using methods in the literature for example the use transcription terminators on the 3' end such as the T7 terminator, ρ-independent terminator, cry element (Gelfand et al. U.S. Pat. No. 4,666,848, issued May 19, 1987) or the TrpE terminator. Furthermore, sequences such as the poly (A) addition signal AATAAA may be added and strategies involving changing the length of the 3' non-coding region (see Gillies, U.S. Pat. No. 5,149,635, issued Sep. 22, 1992.) These techniques can be used to stabilize mRNA for ribozyme, antisense, or protein production purposes.

Specifically, this invention encompasses RNA molecules capable of conferring stability on single stranded RNA represented by the $(X)_n$ and $(X)_{n'}$ of interest which have the structure (SEQ ID NO: 5):

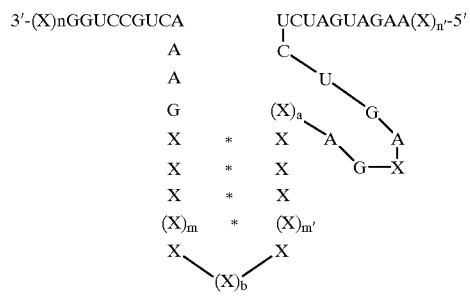

wherein each X represents a ribonucleotide which may be the same or different; wherein each of $(X)_n$ and $(X)_{n'}$ represents an oligonucleotide having a predetermined sequence; wherein each of n and n' represents an integer from 0 to 1000; wherein each * represents base pairing between the ribonucleotides located on either side thereof; wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligoribonucleotide with the proviso that b represents an integer which is greater than or equal to 2.

Another embodiment of the invention is an RNA molecule having the structure (SEQ ID NO: 6):

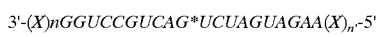

wherein each X represents a ribonucleotide which may be the same or different; wherein G* may be present or absent; and $(X)_n$ and $(X)_{n'}$ are as defined above.

As described above site directed mutagenesis is possible in the GGUCCGUCA and UCUAGUAGAA (SEQ ID NO: 7) respectively in either the TNF-α ribozyme or the TNF-α antisense structure. Because the arms are binding the RNA binding in vivo considerable variations are possible. Compounds missing either the 3' or the 5' arm are also encompassed within the invention describe herein.

In one embodiment of the invention $(X)_n$ or $(X)_{n'}$ encodes at least one ribozyme. The ribozyme may be a hairpin ribozyme, RNAase P, or more preferably a hammerhead ribozyme. In the case wherein $(X)_n$ or $(X)_{n'}$ encodes at least one hammerhead ribozyme it may have the structure (SEQ ID NO: 8):

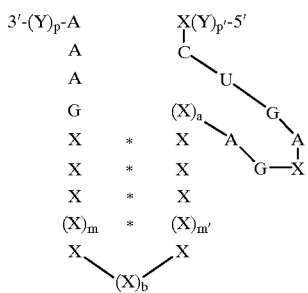

wherein each of X and Y represents a ribonucleotide which may be the same or different; wherein each of $(Y)_p$ and $(Y)_{p'}$ represents an oligonucleotide having a predetermined sequence which is capable of hybridizing with an RNA target sequence to be cleaved; wherein each of p and p' represents an integer which defines the number of ribonucleotides in the oligonucleotide with the proviso that the sum of p+p' is sufficient to allow the ribozyme to hybridize with the RNA target sequence; wherein each * represents base pairing between the ribonucleotides located on either side thereof: wherein each solid line represents a chemical linkage providing covalent bonds between the ribonucleotides located on either side thereof; wherein a represents an integer which defines a number of ribonucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligoribonucleotide with the proviso that b represents an integer which is greater than or equal to 2.

In embodiment of the invention the RNA molecule may have the following structures (SEQ ID NO: 9,10):

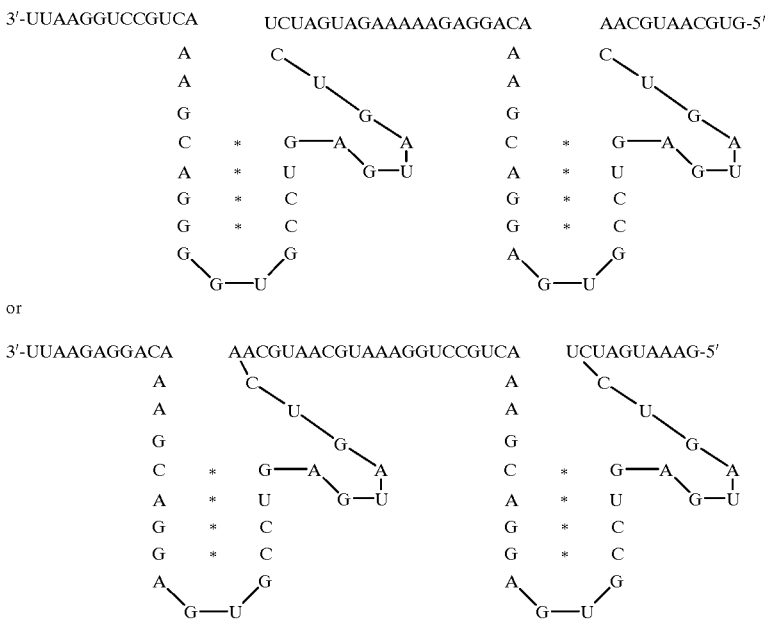

Additional embodiments of the invention may have the following structures (SEQ ID NO: 11–13):

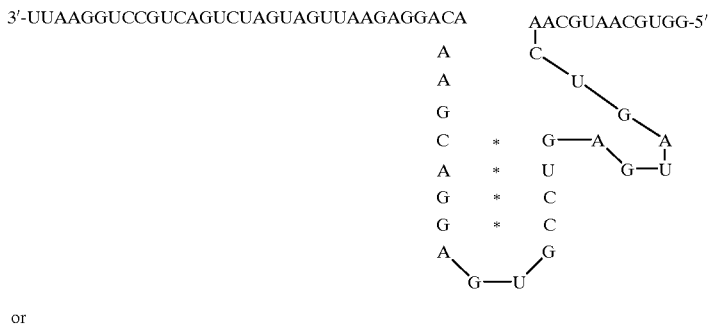

or

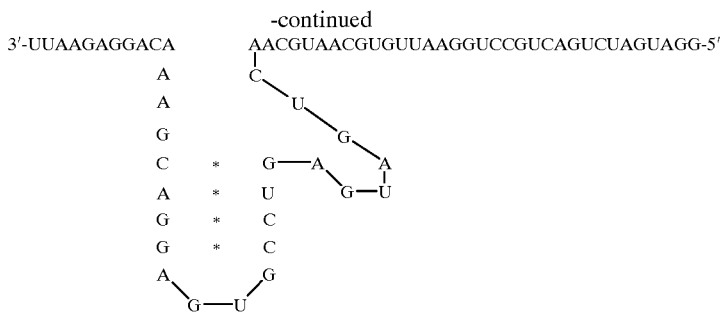

For the specific IL-2 ribozymes above one with skill in the art will recognize that one can change the AAA linker.

Alternatively, $(X)_n$ or $(X)_{n'}$ may have the structure:

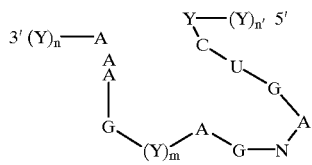

wherein each Y represents a ribonucleotide or a deoxyribonucleotide which is the same or different and may be modified or substituted in its sugar, phosphate or base; wherein $(Y)_n$ and $(Y)_{n'}$ represent oligonucleotides in which n and n' are integers which define the number of nucleotides in the oligonucleotides, such oligonucleotides having predetermined sequences sufficiently complementary to a predefined RNA target sequence to be cleaved to allow hybridization to the RNA target sequence, such predefined RNA target sequence not being present within the compound; wherein N may be adenine, guanine, cytosine or uracil; wherein each solid line represents a chemical linkage providing covalent bonds between the nucleotides located on either side thereof; wherein M represents an integer from 2 to 20; and wherein none of the nucleotides $(Y)_m$ are Watson-Crick base-paired to any other nucleotide within the compound.

Another embodiment of the claimed invention the RNA molecule described above may also be used to stabilize an mRNA which encodes a polypeptide. Particularly, the RNA compounds are useful for the production of proteins of industrial of commercial significance. Many such proteins are either already available commercially or are under commercial development. Example such proteins include human and animal growth hormones, tissue plasminogen activators, erythropoietin, and factor VIII.

The invention may be employed to improve the production of such protein in cell culture, particularly in animal cell culture such as in CHO cells grown in culture and thereby reduce the substantial costs involved in commercial production of such proteins.

Another embodiment on the invention $(X)_n$ or $(X)_{n'}$ a ribozyme capable of cleaving targets. Alternatively, $(X)_n$ or $(X)_{n'}$ is an antisense sequence capable of hybridizing to an RNA indigenous to a mammal or plant and thereby deactivating it (for plants see Shewmaker et al. U.S. Pat. No. 5,107,065, issued Apr. 21, 1992). Further, the targets for the ribozyme or antisense sequence may a viral gene including viral targets such as cytomegalovirus, hepatitis, herpes, HIV, EBV, papilloma virus, cytomegalovirus, rhinovirus, influenza virus, varicella-zoster virus, parainfluenza virus, mumps virus, respiratory syncytial virus, adenovirus, measles virus, rubella virus, human parvovirus, poliovirus, rotavirus, echovirus, arbovirus, human T cell leukemia-lymphoma virus.

The invention also embodies methods of production of the compounds and RNA molecules described above comprising the steps of: (a) ligating into a transfer vector comprised of DNA, RNA or a combination thereof a nucleotide sequence corresponding to said compound; (b) transcribing the nucleotide sequence of step (a) with RNA polymerase; and (c) recovering the compound. The invention also includes transfer vectors, bacterial or phage, comprised of RNA or DNA or a combination thereof containing a nucleotide sequence which on transcription gives rise to the compounds or RNA molecules described above.

Further, many methods have been developed for introducing cloned eukaryotic DNAs into cultured mammalian cells (Sambrook et al. Molecular Cloning: A Laboratory Manual 2ed. Cold Spring Harbor Laboratory Press 1989):

Calcium phosphate- or DEAE-dextran-mediated transfection;

Polybrene;

Protoplast fusion;

Electroporation; and

Direct microinjection into nuclei.

The invention provides a method of treating a disorder associated with over expression of TNF-α which comprises administering to a subject an effective amount of the TNF-α so as to reduce the overexpression of TNF-α and thereby treat the disorder. Such disorders include rheumatic arthritis, AIDS, and autoimmune diseases.

The invention also provides a method of cleavage or deactivation of a specific RNA target sequence using the RNA molecules described above. Such RNA sequences may be indigenous to a mammal or a plant. It is particularly suited for targetting viral genes such as HIV (see Goodchild et al. U.S. Pat. No. 4,806,463, issued Feb. 21, 1989).

In the compounds and methods described herein the respective 5' and 3' termini of the groups $(X)_n$ and $(X)_{n'}$ may be modified to stabilize the endonuclease from degradation. For example, blocking groups may be added to prevent terminal nucleases attack, in particular 3'–5' progressive exonuclease activity. By way of example, blocking groups may be selected from optionally substituted alkyl, optionally substituted phenyl, optionally substituted alkanoyl. Optional substituents may be selected from C1–C5 alkoxy and the like. Alternatively, nucleotide analogues such as phosphothioates, methylphosphonates or phosphoramidates or nucleoside derivatives (such as α-anomers of the ribose moiety) which are resistant to nuclease attack may be employed as terminal blocking groups.

Alternatively, non nucleic acid groups which alter the susceptibility of the endonuclease molecule to other nucleases may be inserted into the 3' and/or 5' end of the endonuclease. For example, 9-amino-acridine attached to the endonuclease may act as a terminal blocking group to generate resistance to nuclease attack on the endonuclease molecules and/or as an intercalating agent to aid endonucleolytic activity. It will be readily appreciated that a variety of other chemical groups, e.g. spermine or spermidine could be used in a related manner.

Endonucleases of this invention may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the endonucleases of the present invention may be associated with RNA binding peptides or proteins which may assist in bringing the endonuclease into juxtaposition with a target nucleic acid such that hybridization and cleavage of the target sequence may take place. Nucleotide sequences may be incorporated into the 5' and 3' ends of the groups $(X)_n$ and $(X)_{n'}$ to increase affinity for substrates. Such additional nucleotide sequences may form triple helices with target sequences (Strobel, S. A., et al., (1991) Nature 350: 172–174 and references therein which are incorporated by reference) which may enable interaction with intramolecularly folded substrate. Alternatively, modified bases (non-natural or modified bases as described in Principles of Nucleic Acid Structure, Supra) bases within the additional nucleotide sequences may be used that will associate with either single stranded or duplex DNA generating base pair, triplet, or quadruplet, interactions with nucleotides in the substrate. Suitable bases would include inosine, 5'- methylcytosine, 5'-bromouracil and other such bases as are well known in the art, as described, for example, in Principles of Nucleic Acid Structure, Supra.

Synthetic preparations of mRNA are well known (see Sambrook et al. Molecular Cloning: A Laboratory Manual 2ed. Cold Spring Harbor Laboratory Press 1989). Mixed DNA-RNA oligomers with modified base pairs for the TNF-α ribozyme can be prepared by commercially available DNA synthesizers such as those produced by Applied Biosystems, Biosearch, or Milligen(see, e.g., Perrault et al, Nature, 344: 565–567 (1990, for derivatives Uhlmann, E. and Peyman, A. Chemical Reviews (1990) 90: 543–584, H-phosphonate monomers see Agrawal et al U.S. Pat. No. 5,149,798).

An "effective amount" as used herein refers to that amount which provides a desired effect in a mammal having given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the oligonucleotide, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multimellar vesicles, erythrocyte ghosts, or spheroplasts. Such compositions will influence the physical state, solubility, stability, rate of in vivo release, and rate of in vivo clearance of the oligonucleotide. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. Possible sustained release compositions include formulation of lipophilic depots (e.g., fatty acids, waxes, oils). Also comprehended by the invention are particulate compositions coated with polymers (e.g., polyoxamers or polyoxamines) and oligonucleotides coupled to antibodies directed against tissue-specific receptors, ligands or antigens or coupled to ligands of tissue-specific receptors. Further, specific nucleotide sequences may be added to target the oligonucleotides of this invention to the nucleus, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, a aerosols, or other inhalants. The oligonucleotides may be encapsulated in a wafer, wax, film or solid carrier, including chewing gums. Permeation enhancers to aid in transport to movement across the epithelial layer are also known in the art and include, but are not limited to, dimethyl sulfoxide and glycols.

This invention is illustrated in the Experimental Detail section which follow. These sections are set forth to aid in an understanding of the invention but are not intended to, and should not be construed to, limit in any way the invention as set forth in the claims which follow thereafter.

EXPERIMENTAL DETAILS

Targeted Ribozymes Cut TNF-α RNA in Vitro

Figure 1:
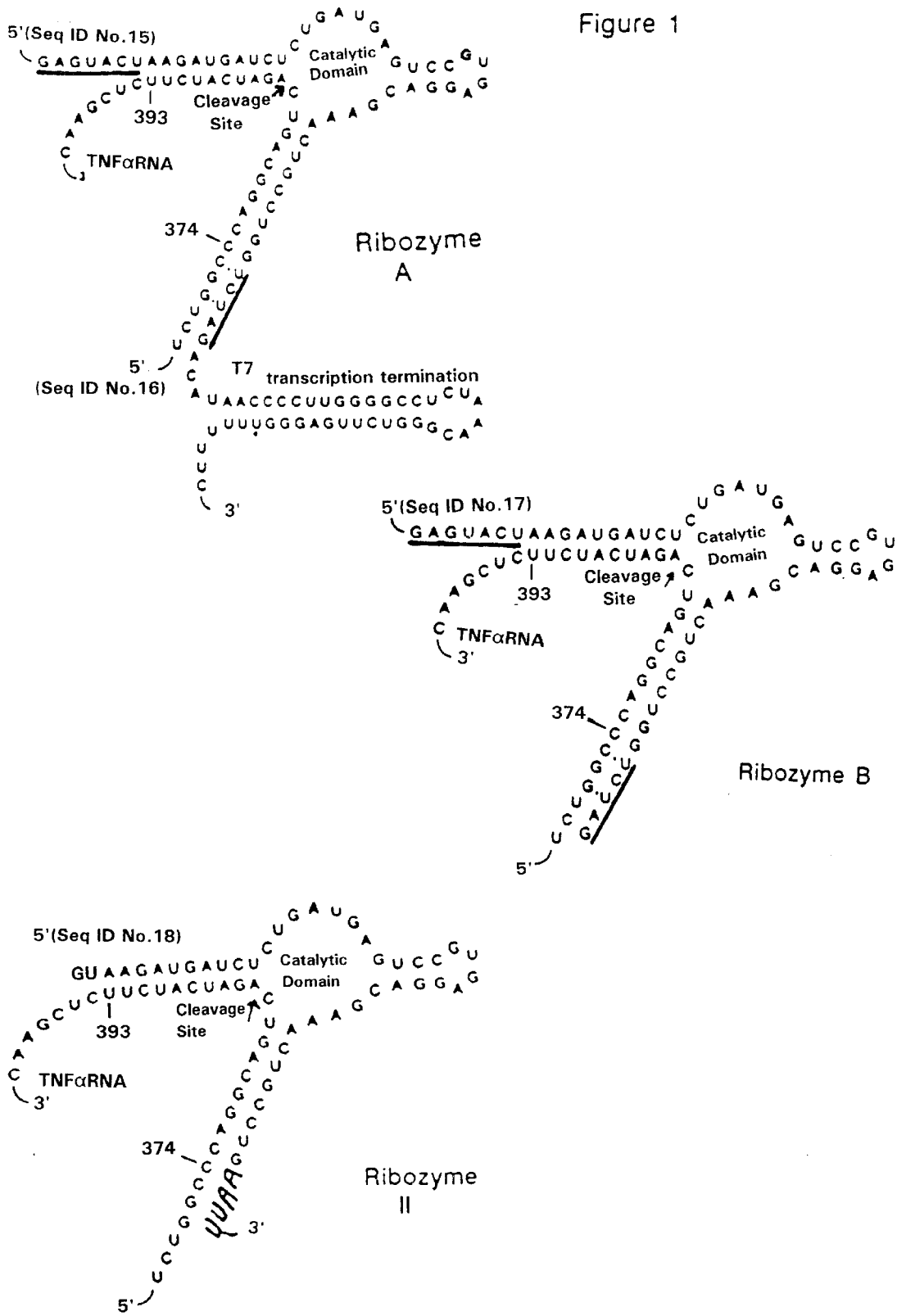
FIG. 1: Base-pairing of ribozyme A, B and II with TNF-α RNA template (SEQ. ID. NO: 15–18)

Three hammerhead ribozymes (Haseloff & Gerlach, 1988) designed to cleave the TNF-α RNA is shown in FIG. 1. Their in vitro activities were studied using as target total RNA extracted from PBMNC after stimulation of TNF-α gene transcription by phorbol 12-myristate 13-acetate (PMA) and concanavalin A (Con A) as described by English et al. (1991). Ribozyme A contained a bacteriophage T7 terminator at its 3' end while ribozyme B did not. Ribozyme II lacked the underlined restriction sites. FIG. 2 shows Ribozyme-mediated RNA cleavage was assayed by gel electrophoresis and Northern blot hybridization using TNF-α probe. The TNF-α RNA fragments cut by ribozyme cleaved the approximately 1800 nucleotide-long target RNA into fragments of 1420 and 380 nucleotides. The sizes of the TNF-α fragments of the TNF-α fragments produced by the ribozymes were consistent with the location of predicted site for cleavage. Thus, ribozymes A and B cleave the TNF-α target in vitro in the presence of unrelated RNAs.

Stability of Ribozymes A, B, and II in Living Cells

Stability of ribozyme A, B and II in living cells is shown in FIGS. 3 and 4. Since the cell membrane presents a substantial barrier to the entry of highly charged, high molecular weight molecules, delivering them to the cytoplasm is a major task. To overcome this, transfection techniques such as cationic liposome-mediated transfection (Malone et al., (1989) Proc. Natl. Acad. Sci., USA 86: 6077–6081), electroporation (Callis et al., (1987) Nucl. Acids. Res. 15: 5823–5831) and microinjection (Rosa et al., (1989) J. Cell. Biol. 109: 17–34) have been developed. Since the liposome-based method appears to be the most versatile, its ability was tested to deliver enough functional ribozyme to successfully cleave TNF-α RNA.

The efficiency of RNA transfection was first measured in HL60 cells, as determined by measurement of cell-associated intact $^{32}$p-labelled RNA. Following transfection with ribozymes, cells were washed with Hank's buffered salt solution (GIBCO). Total RNA was prepared from cells and the RNA species were separated by gel electrophoresis. The radioactivity contained in the ribozyme RNA bands was then determined. The results indicate that the radioactive bands varied from 2 to 4% of the initial RNA added to the liposomes during the transfection period of between 8 and 20 hours. This corresponds to a delivery of approximately 300,00 molecules of ribozyme A per cell.

FIG. 4 shows stability of ribozymes A, B, and II. Ten million human HL60 cells (ATCC CCL 240), growing in log phase in RPMI 1640 supplemented with 20% (v/v) fetal calf serum (FCS), were used for RNA transfection. Cells were washed twice with serum-free medium. A drop (5 ml) of serum free medium was added to polystyrene tubes followed by 35 μg of lipofectin (Bethesda Research Laboratories). 10 μg of carrier RNA (*E. coli.* tRNA). $3 \times 10^6$ disints min of $^{32}$p-labelled capped ribozyme A, B or II (5 μg). The mixture was immediately mixed. The cells were resuspended in a mixture of serum-free medium lipofectin/RNA/carrier RNA and returned to the incubator for 20 h. Following transfection cells were washed 3 times with Hank's buffered saline solution and then returned to the incubator with RPMI supplemented with 20% FCS. Cells ($10^6$) were harvested at the times indicated above each lane, and total RNA was prepared and analyzed by 15% polyacrylamide gel with 7 M-urea. The RNA samples used for transfection are indicated at the top of FIG. 4. A sample (50 μM) of labelled, capped ribozyme A was used to transfect HL60 cells for 20 h. Cells were washed 3 times, and the nuclear and cytoplasmic RNAs were prepared and analyzed by gel electrophoresis. For preparation of cytoplasmic and nuclear fractions, the cells were homogenized in 10 mM-Tris.HCl (pH 7·5). 5 mM-KCl, 140 mM-NaCl, 5 mM-dithiothreitol and 04% (w/v) Nonidet P40 for 10 min at 4° C. and the nuclei were collected by centrifugation at 800 g for 5 min. RNA in the supernatant fluid was precipitated and saved as the cytoplasmic fraction. The nuclei were processed as described by Chomezynski & Sacchi (Anal. Biochem (1987) 162: 156–160) for total RNA preparation. The arrow indicated the position of ribozyme A monomer. RNA quantification. The amount of radioactivity in the ribozyme bands shown in (a) was determined and expressed as a percentage of the radioactivity present immediately after 20 h transfection time.

FIG. 5 Shows Activity of Ribozymes in Vivo

Ribozymes and antisense RNA activities in HL60 cells (a) were analyzed after a transfection period (20 h). Following transfection with ribozyme A or antisense RNA, cells were stimulated for 6 h to express TNF-α. RNA was extracted, separated by gel electrophoresis through a 1–2% (w/v) agarose form-aldehyde gel, and detected by Northern blotting with radioactive probe for the TNF-α gene. After hybridization with RNAα probe, the filter was stripped and then hybridized with an actin probe (British Biotechnology Limited). In the case of PBMNC. (b) cells were separated (Sioud et al., Scand. J. Immunol. (1990 31: 415–421) and washed 4 times with Hank's buffered saline solution and 3 times with serum-free medium. Cells ($10^6$) were transfected and processed as HL60 cells. Lanes 1 and 4, controls (transfected only with carrier RNA); lane 2, antisense RNA; lanes 3 and 5, ribozyme A. This auto-radiogram was overexposed to display the TNF-α signal in ribozyme A lanes. (c) Radioimmunoassay to TNF-α protein. The amount of TNF-α protein present in the media was determined using the TNF-α [$^{125}$I] assay system (Amersham). Lanes 1 to 5 correspond to lanes 1 to 5 in FIG. 5(a) and (b), respectively. Destruction of Endogenous TNF-α RNA in Vivo by Ribozymes Experiments were performed to determine if ribozyme A could eliminate its target following RNA transfection. A preliminary time-course study of TNF-α RNA synthesis in HL60 cells indicated that TNF-α RNA could be detected after two hours of stimulation by PMA and ConA, reaching maximal expression after four to six hours. Cells were transfected with ribozymes, stimulated with PMA and ConA for six hours, and total RNA was extracted and analyzed by Northern blotting using a TNF-α probe. Since the TNF-α and actin mRNA have approximately the same electrophoretic mobility, the same blot was hybridized with the actin probe after stripping. Data derived from densitometric scans of underexposed film indicated that the TNF-α signal was reduced by 40% (FIG. 5(a), antisense lane) and 90% (FIG. 3(a), ribozyme A lane). In addition, a radioimmunoassay was used to measure TNF-α protein in the culture medium. This system has major advantages over bio-assays in that it is specific for TNF-α. The data indicates that HL60 stimulated with PMA and ConA secrete as much as 1000 fmol of TNF-α per ml but only 150 and 400 when cells are transfected with ribozyme A and antisense, respectively (FIG. 5(b)).

Since the effect of antisense RNA is less than that of ribozyme A and since both ribozyme A and the antisense RNA were present inside the cells at similar concentrations (data not shown), we suggest that part of the activity of ribozyme A is due to its ability to cleave RNA. Ribozyme-mediated RNA cleavage in vivo has been observed in eukaryotic cells (Saxena & Ackerman, J. Biol. Chem. (1990) 265: 17106–17109).

In this case no cleavage products were seen. As suggested previously (Cotten & Birnstiel, 1989; Sarver et al., 1990; Sioud & Drlica, 1991) the products of ribozyme-mediated cleavage are probably degraded by cellular nucleases (the 5' fragment, although capped at its 5' end, is expected to be rapidly degraded by 3'→5' exonucleases).

The same conditions were used to deliver ribozyme A to PBMNC. As can be seen from FIG. 5(a) and (b), ribozyme A reduced the amount of TNF-α RNA by 80% and the TNF-α protein by 70% raising the possibility that liposome-mediated RNA transfection offers a way to deliver ribozymes to wide variety of cell types. During analysis, ribozyme B appears to induce a similar reduction in TNF-α mRNA as ribozyme A (data not shown). Thus, the addition of T7 transcription terminator may decrease the specific activity of ribozyme A.

FIG. 6 Shows Cellular Distribution of TNF-α Ribozymes

The TNF-α ribozymes (FIG. 1) were unusually stable. They could be detected inside human cells for seven days, while normally, the ribozymes are unstable in human cells see FIG. 4. Although a cell fractionation study indicated that TNF-α ribozymes can be recovered from the cell, it did not address the possibility that a major portion of the ribozyme was sequestered in places inaccessible to cellular nucleases. To address this question cells were transfected with Digoxigenin labelled ribozymes. After 72 hours post transfection microscope slides were prepared and then the ribozyme were detected by anti-Digoxigen-fluoreceinFab conjugate as describe in materials and methods. Data present in FIGS. 5

A and B indicated that the stabilization effect was not due to any cellular compartmentalization, because upon immunofluorescence staining of the ribozyme, the whole cell acquired the fluorescence. See FIG. 6(a) and FIG. 6(B).

FIG. 7 Shows Electrophoretic Mobility Shift Analysis of TNF-α Ribozymes with Cellular Extracts The initial hypothesis was that the ribozyme directed against this particular site of tumor necrosis factor are protected by certain cellular factors such as proteins. If proteins were binding to the ribozymes and protecting them from degradation, mobility shift experiments should detected them. During initial experiments, carried out with HL60 cells cytoplasmic proteins revealed that the complexes formation were not inhibited by the presence of polydC dI and the tRNA in the reaction mixture. In these experiments there was still considerable degradation of the ribozyme due to the nucleases present in the extract. When Rnasin was then added to incubation mixture to lower the effect of ribonuclease a much greater portion of the input RNA was captured in the major complex (FIG. 7b lanes 2, 3 and 4). When, cytoplasmic extracts from PBMN cells have used, the complex with high electrophoretic mobility was also detectable (FIG. 7b lanes 6, 7), suggesting that the protein binds to the ribozyme is a common protein to all cell types. The complexes formed in the presence or absence of RNasin had identical mobilities indicating that the proteins bind to the full length. Furthermore, the ribozyme recovered from the complex following phenol extraction corresponds to the full length ribozyme (FIG. 7b lane 8).

Complex Formation is Specific for TNF-α Ribozymes

Adding tRNA to the reaction did not diminish the amount of complex formed, suggesting some specific binding to the ribozyme. This specificity of binding was confirmed by the competition assays (FIG. 8). In contrast to tRNA and Polvd CdI, cold ribozyme competes with hot ribozymes for complex formation. Interesting complexes formation was not observed with hammerhead ribozymes directed at mRNA of IL-2 or integrase of HIV. This indicates that the binding was not due to the catalytic domain of TNF-α ribozymes. IL-2 ribozyme was not stable inside the cells as TNF-α ribozyme and does not exhibit this binding phenomenon. Thus, it is possible that this binding is responsible for the in vivo stability of the TNF-α ribozymes.

TNF-α Ribozyme Confers stability to Other Ribozymes

Even before characterizing this RNA elements that protects the TNF-α from degradation the possibility was tested that it could be tagged to other RNAs and stabilize them. The TNF-α ribozyme was linked to the 3'end of IL-2 ribozyme (FIG. 9) which was unstable alone. As shown in FIG. 10A and B, the IL-2 ribozyme did not form complexes on its own with any cellular factor in our conditions. However the connection conferred stability to the joint ribozyme. This double ribozyme binds to the cellular protein (FIG. 10). Since the TNF-α and IL-2 ribozymes differ only in the nucleotide sequence complementary to their RNA targets, that region of TNF-α is likely to be responsible for the complex formation and intracellular stability. The TNF-α ribozyme was linked in the IL-2 ribozyme forming a chimeric bis ribozyme which conferred the stability of the TNF-α ribozyme itself. Furthermore, the antisense TNF-α RNA was linked in the IL-2 ribozyme and conferred stability.

The in Vivo Activity of Protected and Unprotected IL-2 Ribozymes

We know that the inhibition of TNF-α gene expression by antisense or the ribozyme does not significantly effect the IL-2 gene expression. So the effect of the double ribozyme (IL-2 ribozyme linked to TNF-α ribozyme) on IL-2 gene expression could be investigated precisely.

Activity of Ribozymes Quantification of IL-2 Following Ribozymes Transfection

PBMNC were transfected with IL-2 ribozyme, IL-2 ribozyme linked to TNF-α ribozyme or IL-2 ribozyme linked to TNF-α antisense for 2 hours. Following transfection the cells were stimulated with PHA for 20 hours and then the IL-2 contained in the media was determined using the CTLL2 system. Briefly, series of dilution (1/2 to 1/16) were prepared from supernatant obtained from controls and cells transfected with ribozymes. One 100 µl from each dilution (triplicated) were added to 5,000 CTLL2 cells. (in 20 µl media). After 20 hours the cells were pulsed with 3H-thymidine for 4 hours, harvested and then the DNA associated radioactivity were determined.

|  | control | +IL-2 ribozyme | +IL-2 linked to TNF-α R | IL-2 linked to TNF-α A |
|---|---|---|---|---|
| CPM | 871 | 421 | 396 | 547 |
| % of inhibition | 0 | 52 | 55 | 38 |

R = ribozyme; A = antisense for unknown reasons the CTLL2 cells growth slowly in the media which we have used.

CONCLUSION

Thus we have demonstrated that TNF-α ribozymes are unusually stable inside human cells. This phenomenon is not easily explained in terms of intracellular location, since the ribozyme appear to be distributed throughout the cells (FIG. 6). A significant fraction of the ribozyme was recovered as complex having reduced electrophoretic mobility. Suppression of the ribonucleases by RNasin increases the recovery of the complexes from cytoplasmic extracts. Addition of tRNA had no competitive effect. Inhibition was of complex formation was obtained with only cold ribozyme. Neither integrase nor IL-2 ribozymes formed detectable complexes. Thus, the binding is specific for TNF-α ribozyme. The IL-2 ribozyme showed a reduced intracellular stability compared to the TNF-α ribozyme, raising the possibility that complexes formation is related to the stability.

The linkage of TNF-α ribozyme to IL-2 ribozyme both increased stability and conferred the ability to the double ribozyme to form complexes. Further, the linked ribozymes were active.

Since the TNF-α, IL-2 and integrase differed in the regions complementary to their targets, therefore this region is responsible for protein binding and the complex formation. This region is believed to confer resistance to nucleases.

What is claimed is:

1. A compound having the structure (SEQ ID NO: 1):

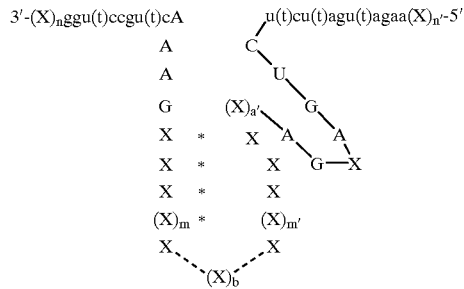

wherein each X represents a ribonucleotide which is the same or different and may be modified in its phosphate;

wherein each of A, C, U, and G represents a ribonucleotide and a, c, u(t), and g represents a ribonucleotide or deoxyribonucleotide which may be modified in its phosphate;

wherein each of $(X)_n$ and $(X)_{n'}$ represents an oligonucleotide having a predetermined sequence;

wherein each of n and n' represents an integer;

wherein each * represents base pairing between the nucleotides located on either side thereof;

wherein each solid line represents a chemical linkage providing covalent bonds between the nucleotides located on either side thereof;

wherein a' represents an integer which defines a number of ribonucleotides with the proviso that a' may be 0 or 1 and if 0, the A located 5' of $(X)_{a'}$ is bonded to the X located 3' of $(X)_{a'}$;

wherein each of m and m' represents an integer which is greater than or equal to 1;

wherein each of the dashed lines independently represents either a chemical linkage providing covalent bonds between the nucleotides located on either side thereof or the absence of any such chemical linkage; and wherein $(X)_b$ represents an oligonucleotide which may be present or absent with the proviso that b represents an integer which is greater than or equal to 2 if $(X)_b$ is present.

2. The compound of claim 1, wherein each X represents a ribonucleotide; wherein each of A, C, U, and G represents a ribonucleotide and each of a, c, u(t), and g represents a ribonucleotide.

3. The compound of claim 1 having the structure (SEQ ID NO: 26):

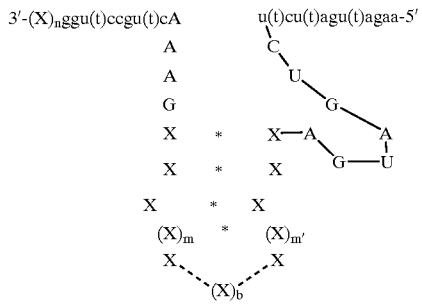

wherein each X represents a ribonucleotide which is the same or different and may be modified or substituted in its sugar, phosphate or base;

wherein each of A, C, T, and G represents a ribonucleotide and a , c, u(t), and g represents a ribonucleotide or deoxyribonucelotide which may be unmodified or modified or substituted in its sugar, phosphate or base;

wherein $(X)_n$ represents an oligonucleotide having a predetermined sequence wherein n represents an integer;

wherein each * represents base pairing between the nucleotides located on either side thereof;

wherein each solid line represents a chemical linkage providing covalent bonds between the nucleotides located on either side thereof;

wherein each of m and m' represents an integer which is greater than or equal to 1;

wherein each of the dashed lines independently represents either a chemical linkage providing covalent bonds between the ribonucleotides located on either side thereof or the absence of any such chemical linkage; and wherein $(X)_b$ represents an oligonucleotide which may be present or absent with the proviso that b represents an integer which is greater than or equal to 2 if $(X)_b$ is present.

4. The compound of claim 3 having the structure (SEQ ID NO: 3):

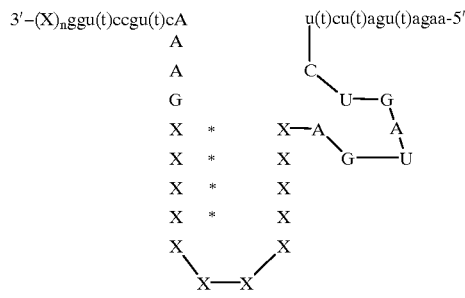

wherein each X represents a ribonucleotide which is the same or different and may be modified or substituted in its sugar, phosphate or base;

wherein A, C, T, and G represent ribonucleotides and a, c, u(t), and g represent ribonucleotides or deoxyribonucleotides which may be unmodified or modified or substituted in its sugar, phosphate or base;

wherein $(X)_n$ represents an oligonucleotide having a predetermined sequence wherein n represents an integer;

wherein each * represents base pairing between the ribonucleotides located on either side thereof; and wherein each solid line represents a chemical linkage providing covalent bonds between the ribonucleotides located on either side thereof.

5. The compound of claim 4 having the structure (SEQ ID NO: 5):

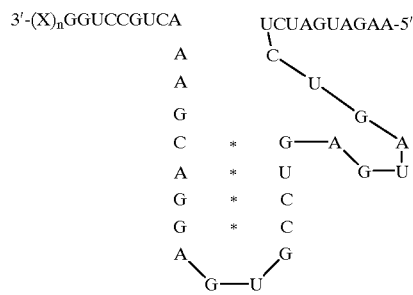

wherein each X represents a ribonucleotide which is the same or different; wherein A, C, U, and G represent ribonucleotides;

wherein $(X)n$ represents an oligoribonucleotide having a predetermined sequence wherein n represents an integer;

wherein each * represents base pairing between the ribonucleotides located on either side thereof; and wherein each solid line represents a chemical linkage providing covalent bonds between the ribonucleotides located on either side thereof.

6. A compound having the structure:

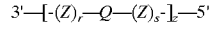

wherein Q represents the compound of claim 1;

wherein each Z represents a ribonucleotide or a deoxyribonucleotide which is the same or different and may be modified or substituted in its sugar, phosphate or base;

wherein each of r and s represents an integer which may be greater than or equal to 0; and wherein z represents an integer greater than or equal to 1.

7. A method for producing the compound of claim 2, which comprises the steps of:

(a) ligating into a transfer vector comprised of DNA, RNA or a combination thereof a nucleotide sequence corresponding to said compound;

(b) transcribing the nucleotide sequence of step (a) with RNA polymerase; and (c) recovering the compound.

8. A transfer vector consisting of RNA or DNA containing a nucleotide sequence which on transcription gives rise to the compound of claim 2.

9. A transfer vector according to claim 8 which is a bacterial plasmid or phage DNA.

10. A prokaryotic or eukaryotic cell containing a nucleotide sequence which on transcription gives rise to the compound of claim 2.

* * * * *